(12) United States Patent
Humblot et al.

(10) Patent No.: US 9,353,054 B2
(45) Date of Patent: May 31, 2016

(54) HYDROTREATING CATALYST SULPHIDING AGENT AND ITS USE FOR IN SITU AND EX SITU PRESULPHIDATION

(75) Inventors: Francis Humblot, Lanneplaa (FR); Paul-Guillaume Schmitt, Lescar (FR); Georges Fremy, Sauveterre de Beam (FR)

(73) Assignee: ARKEMA FRANCE, Colombes (FR)

( * ) Notice: Subject to any disclaimer, the term of this patent is extended or adjusted under 35 U.S.C. 154(b) by 0 days.

(21) Appl. No.: 12/858,647

(22) Filed: Aug. 18, 2010

(65) Prior Publication Data

US 2011/0005974 A1    Jan. 13, 2011

Related U.S. Application Data

(63) Continuation of application No. 11/961,164, filed on Dec. 20, 2007, now abandoned.

(60) Provisional application No. 60/939,152, filed on May 21, 2007.

(30) Foreign Application Priority Data

Dec. 22, 2006  (FR) ...................................... 06 55884
Sep. 3, 2007   (FR) ...................................... 07 57330

(51) Int. Cl.
  *C10G 29/28*   (2006.01)
  *C07C 321/14*  (2006.01)
  *B01J 37/20*   (2006.01)
  *C01G 51/04*   (2006.01)
  *C01G 53/04*   (2006.01)
  (Continued)

(52) U.S. Cl.
  CPC ............... *C07C 321/14* (2013.01); *B01J 37/20* (2013.01); *C01G 51/04* (2013.01); *C01G 53/04* (2013.01); *C10G 45/08* (2013.01); *B01J 23/882* (2013.01); *C01P 2006/80* (2013.01)

(58) Field of Classification Search
  None
  See application file for complete search history.

(56) References Cited

U.S. PATENT DOCUMENTS 2,993,938 A   7/1961   Bloch et al.
3,016,347 A   1/1962   O'Hara
(Continued)

FOREIGN PATENT DOCUMENTS

EP   976726   2/2000
FR   64429    11/1982
(Continued)

OTHER PUBLICATIONS

Hallie, H., Experience reveals best presulfiding techniques for HDS and HDN catalysts, Oil and Gas Journal, Dec. 20, 1982, pp. 69-74.
(Continued)

*Primary Examiner* — Colin W Slifka
(74) *Attorney, Agent, or Firm* — Smith, Gambrell & Russell, LLP

(57) ABSTRACT

The present invention relates to a sulphiding agent for a hydrotreating catalyst which makes possible faster sulphiding of the catalyst but which also makes possible to very significantly limit solid deposits, in particular of sulphur.
The sulphiding agent according to the invention is essentially composed of diethyl disulphide (DEDS) or dipropyl disulphide(s) (DPDS) or dibutyl disulphide(s) (DBDS) and can be employed in "in situ" and "ex situ" presulphidation processes.

20 Claims, 1 Drawing Sheet

(51) Int. Cl.
*C10G 45/08* (2006.01)
*B01J 23/882* (2006.01)

(56) References Cited

U.S. PATENT DOCUMENTS

| | | |
|---|---|---|
| 3,140,994 A | 7/1964 | Derr, Jr. et al. |
| 3,527,839 A | 9/1970 | Barnett et al. |
| 3,530,200 A | 9/1970 | Glockner |
| 3,732,155 A | 5/1973 | Cecil et al. |
| 4,098,682 A | 7/1978 | O'Hara |
| 4,132,632 A | 1/1979 | Yu et al. |
| 4,172,027 A | 10/1979 | Ham et al. |
| 4,176,087 A | 11/1979 | Dew et al. |
| 4,334,982 A | 6/1982 | Jacquin et al. |
| 4,397,739 A | 8/1983 | Jacquin et al. |
| 4,530,917 A * | 7/1985 | Berrebi ............ 502/220 |
| 4,725,569 A | 2/1988 | Tuszynski et al. |
| 4,725,571 A | 2/1988 | Tuszynski |
| 4,983,558 A | 1/1991 | Born et al. |
| 5,820,749 A | 10/1998 | Haluska et al. |
| 6,639,110 B2 | 10/2003 | Fremy |
| 6,743,951 B2 | 6/2004 | Fremy |
| 2004/0112795 A1 * | 6/2004 | Brun et al. ............ 208/213 |

FOREIGN PATENT DOCUMENTS

| | | |
|---|---|---|
| FR | 2627104 | 8/1989 |
| GB | 1309457 | 3/1973 |
| JP | 3138059 | 12/1993 |
| WO | WO 88/05338 | 1/1988 |
| WO | WO 01/96499 | 12/2001 |

OTHER PUBLICATIONS

Hirabayashi, T., et al., "Thermische Zersetzung Offenkettiger Dialkyl-sulfide, -disulfide and -diselenide", Chem. Ber., 115, 483-491 (1982).

* cited by examiner

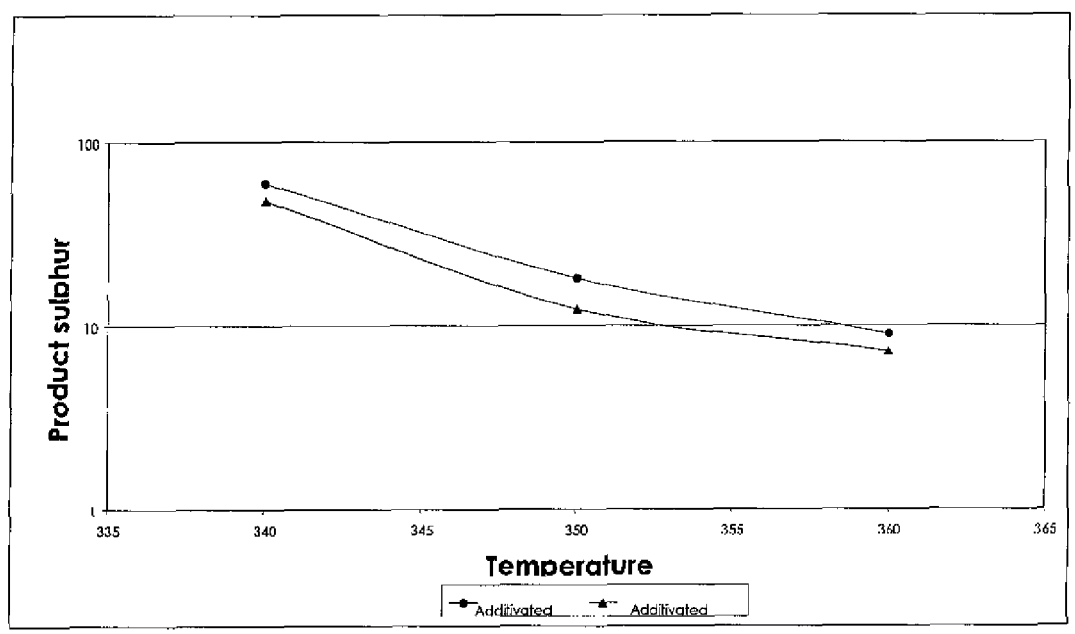

HYDROTREATING CATALYST SULPHIDING AGENT AND ITS USE FOR IN SITU AND EX SITU PRESULPHIDATION

CROSS-REFERENCE TO RELATED APPLICATIONS

The present application is a continuation of U.S. application Ser. No. 11/961,164 filed on Dec. 20, 2007

FIELD OF THE INVENTION

The present invention relates to the field of the hydrotreating of hydrocarbon feedstocks and has more particularly as subject-matter a process for the presulphidation of the catalysts used for this purpose.

BACKGROUND OF THE INVENTION

The catalysts for the hydrotreating of hydrocarbon feedstocks to which the present invention relates are used, under appropriate conditions, for converting, in the presence of hydrogen, organosulphur compounds to hydrogen sulphide, which operation is known as hydrodesulphurization (HDS), and for converting organonitrogen compounds to ammonia in an operation known as hydrodenitrogenation (HDN).

These catalysts are generally based on metals from Groups VI B and VIII of the Periodic Table of the Elements, such as molybdenum, tungsten, nickel and cobalt. The most commonly used hydrotreating catalysts are formulated from cobalt-molybdenum (Co—Mo), nickel-molybdenum (Ni—Mo) and nickel-tungsten (Ni—W) systems, deposited on porous inorganic supports, such as aluminas, silicas or silicas/aluminas. These catalysts, manufactured industrially at very large tonnages, are supplied to the user in their oxide forms (for example, catalysts formed of cobalt oxide-molybdenum oxide on alumina, symbolized by the abbreviation: Co—Mo/alumina).

However, these catalysts are active in hydrotreating operations only in the form of metal sulphides. This is why, before being used, they have to be sulphided.

As regards the activation of hydrotreating catalysts, the sulphidation of these catalysts is an important stage in maximizing their performances in EMS and in HDN. As is indicated by the authors of Hydrotreating Catalysis (Catalysis, vol. 11, 1996, p. 25, edited by J. R. Anderson and M. Boudart), practical experience has shown that the sulphidation procedure can have a significant influence on the activity and the stability of the catalyst and great efforts have been devoted to improving the sulphidation procedures.

The most direct method for the sulphidation of a catalyst consists in treating the latter with hydrogen sulphide mixed with hydrogen. However, this method, which has formed the subject-matter of numerous patents (U.S. Pat. No. 3,016,347, U.S. Pat. No. 3,140,994, GB 1 309 457, U.S. Pat. No. 3,732,155, U.S. Pat. No. 4,098,682, U.S. Pat. No. 4,132,632, U.S. Pat. No. 4,172,027, U.S. Pat. No. 4,176,087, U.S. Pat. No. 4,334,982, FR 2 476 118), exhibits major disadvantages (acute toxicity, difficulty in supplying $H_2S$) which do not allow it to be employed on all industrial sites.

Industrial procedures for the sulphidation of catalysts are generally carried out under hydrogen pressure with liquid feedstocks already comprising sulphur compounds as sulphiding agents. The main method used in the past by refiners consisted in sulphiding the catalysts with sulphur-comprising petroleum feedstocks but this technique exhibited significant disadvantages because of the difficulty of converting the sulphur compounds to hydrogen sulphide. In order to prevent the catalysts being reduced by the hydrogen, the sulphidations, begun at low temperature, had to be taken slowly to high temperature in order to obtain complete sulphidation of the catalysts.

Sulphur-comprising additives have been provided for improving the sulphidation of the catalysts. The method consists in incorporating a sulphur compound (spiking agent) in a feedstock, such as a naphtha, or in a specific fraction, such as a VGO (vacuum gas oil) or an LGO (light gas oil).

The use of sulphur compounds in the non-oxidized form was claimed for the first time in U.S. Pat. No. 3,140,994, in particular: carbon disulphide, thiophene, mercaptans and organic sulphides, in particular dialkyl disulphides or diaryl disulphides, dimethyl disulphide (DMDS) being exemplified.

EP 64 429 describes an effective method for sulphidation by means of a sulphidation feedstock composed of a mixture of at least one sulphur compound and a hydrocarbon feedstock and of a specific temperature profile; mention is made, among sulphur compounds, of carbon disulphide, mercaptans, thiophene compounds, (di)sulphides and hydrogen sulphide, dimethyl disulphide (DMDS) being particularly preferred for the sulphidation of the catalysts and with dimethyl disulphide is described in the patent.

H. Hallie (Oil and Gas Journal, Dec. 20, 1982, pp 69-74) has reviewed these procedures for sulphidation under hydrogen which are carried out directly in hydrotreating reactors. These various techniques for the sulphidation of catalysts, known as "in-situ" techniques, have been compared and studies have shown that sulphidation with a liquid feedstock to which has been added a sulphiding agent (spiked feedstock) which has the property of decomposing at low temperature is the best sulphidation technique. The technique without an additional sulphiding agent (nonspiked feedstock) gives a less active sulphided catalyst. The sulphiding agent which it is preferred to add to the feedstock is dimethyl disulphide.

It is known to a person skilled in the art that dialkyl disulphides can be used as sulphiding agents; however, only dimethyl disulphide has been explicitly mentioned as sulphiding agent, dimethyl disulphide moreover being the reference sulphiding agent in the industry to date.

Organic polysulphides have also been recommended as sulphiding agents for the sulphidation of catalysts. U.S. Pat. No. 4,725,569 describes the use of an organic polysulphide of $R_xR'$ type (R and R' being $C_1$-$C_{20}$ alkyl groups which can be identical or different, with x between 2 and 8, DMDS being excluded) which consists in impregnating the catalyst at ambient temperature with a solution comprising the polysulphide, in subsequently removing the inert solvent and, finally, in carrying out the sulphidation, under hydrogen, of the catalyst charged to the hydrotreating reactor.

EP 298 111 describes a process for the sulphidation of a catalyst by simultaneously passing hydrogen and a hydrocarbon feedstock comprising a sulphiding agent of formula $RS_nR'$ (R and R' being $C_1$-$C_4$ alkyl radicals which can be identical or different, with n between 3 and 10).

WO 01/96499 describes the use as sulphiding agent of mixtures of disulphides resulting from an LPG (liquefied petroleum gas) desulphurization unit of an oil refining unit, the caustic and sodium compounds having been removed from these mixtures. These mixtures of disulphides generally consist, to greater than 98%, of dimethyl disulphide, diethyl disulphide and ethyl methyl disulphide.

EP 0 976 726 describes a composition based on DMDS with a masked odour comprising up to 1% by weight of an odour-masking agent chosen from vanillin, ethyl vanillin and some esters. This masking is effective only if the content of impurities in the DMDS is limited, typically less than 500 ppm of methyl mercaptan, less than 1% of dimethyl sulphide.

It is known to a person skilled in the art that alkyl polysulphides $RS_xR'$ (x being the mean sulphur value and x≥3) decompose at a lower temperature than alkyl disulphides, such as DMDS, which exhibits the advantage of making possible faster sulphidation of the catalysts, an advantage which the industry turns to good account. However, the major disadvantage of polysulphides, also well known in the industry, is the formation of solid sulphur and/or of a solid deposit which is generated during the heat treatment for activation of the catalyst; the solid sulphur and/or the solid deposit can be deposited in the various components of the refinery and thus create blockages which are very harmful to the operation of the industrial unit. Although polysulphides decompose at a lower temperature than alkyl disulphides, the formation of a solid deposit and/or of solid sulphur related to their use represents a problem for refiners who their prefers dimethyl disulphide, which remains the reference sulphiding agent in the industry.

Novel techniques for the sulphiding of catalysts comprising two stages have recently been proposed. In a first stage, referred to as "ex situ", the catalyst is preactivated in the absence of hydrogen outside the refinery after having been impregnated with a sulphiding agent.

EP 130 850 describes a process for the ex situ presulphidation of a catalyst which consists in treating the said catalyst using at least one sulphiding agent of typical formula $RS_nR'$ (R and R' being $C_1$-$C_{150}$ organic radicals (alkyl, naphthenic, aryl, alkylaryl, arylalkyl) which may be identical or different, with n between 3 and 20) used in solution in a solvent; the catalyst in the oxide form is impregnated with a solution of organic polysulphides (for example TPS 37 or TNPS, sold by Arkema), preferably in a hydrocarbon of white spirit type. This preliminary stage of incorporation in the catalyst of a sulphur compound of specific nature is completed by heat treatment of the catalyst in the absence of hydrogen at temperatures not exceeding 150° C. This operation has the effect of removing the organic solvent and of ensuring the attachment of the sulphur to the catalyst via organic polysulphides. At this presulphidation stage, the catalyst is stable in air and can be handled without specific precautions. It is supplied in this state to the user who, after charging to the hydrotreating reactor, can complete the sulphidation of the catalyst under hydrogen for the complete conversion of the metals to metal sulphides in the hydrotreating reactor in the presence of hydrogen. The "ex situ" techniques currently developed on the industrial scale use, as sulphur-comprising products, organic polysulphides or sulphur.

Other organic polysulphide compounds, with different structures, have also been proposed for the "ex situ" presulphidation of catalysts. The products recommended in FR 2 627 104 and EP 329 499 have the general formula R'—($S_y$—R—$S_x$—R—$S_y$)—R' and are obtained from olefins and sulphur chloride by a series of successive stages which involve a reaction with an organic monohalide followed by a reaction with an alkaline polysulphide. In EP 338 897, the claimed products are synthesized from olefins and sulphur chloride with an additional reaction with an alkaline mercaptide or an alkaline polysulphide mercaptate.

BRIEF DESCRIPTION OF THE DRAWING

FIG. 1 is a graph of Product sulphur vs. Temperature

DETAILED DESCRIPTION OF THE INVENTION

The present invention relates to a novel sulphiding agent which has the advantage not only of decomposing at a lower temperature than dimethyl disulphide, regarded as the reference sulphiding agent of the industry, making possible more rapid sulphidation of the catalyst, but also of very significantly limiting solid deposits, in particular of sulphur, in comparison with polysulphides.

The sulphiding agent according to the invention consists essentially of diethyl disulphide (DEDS) or of dipropyl disulphide(s) (DPDS) or dibutyl disulphide(s) (DBDS); it exhibits the advantage of decomposing at a lower temperature than dimethyl disulphide but also of not forming a solid deposit, in particular related to sulphur, unlike polysulphides.

According to a preferred form of the invention, the sulphiding agent consists essentially of DEDS.

According to a preferred form of the invention, the sulphiding agent consists essentially of DPDS.

According to a preferred form of the invention, the sulphiding agent consists essentially of DBDS.

Within the meaning of the present invention, the expression "consists essentially of" means comprises less than 20 000 ppm of impurities, preferably less than 10 000 ppm of impurities and advantageously less than 5000 ppm of impurities. The term "impurities" is understood to mean traces of one or more sulphides which can be represented by the formula $RS_nR'$ with n representing the mean sulphur value ranging from 1 to 10 and R and R' representing H or a $C_1$-$C_{24}$ linear or branched, aryl, cycloalkyl or alkyl chain, such as, for example, DMDS, dimethyl sulphide, methyl mercaptan, ethyl mercaptan, DPDS and/or DBDS when the sulphiding agent consists essentially of DEDS.

The terms "dipropyl disulphide(s) (DPDS)" and "dibutyl disulphide(s)" are understood to mean the isomer or isomers of dipropyl disulphide and dibutyl disulphide respectively, for example n-propyl and/or isopropyl disulphide, n-, iso- and/or tert-butyl disulphide.

According to a preferred embodiment, the sulphiding agent according to the invention additionally comprises at least one scenting base and/or one odour-masking agent chosen, for example, from the odour maskers, alone or as a mixture, described in EP 0 976 726, such as, in particular, vanillin, ethyl vanillin or esters of formula $R^1CO_2R^2$ in which $R^1$ represents a linear or branched hydrocarbon radical comprising from 1 to 4 carbon atoms which is optionally unsaturated and $R^2$ represents a linear, branched or cyclic hydrocarbon radical comprising from 2 to 8 carbon atoms which is optionally unsaturated.

In general, the content of masking agent(s) and/or scenting base is less than or equal to 1% by weight of the total weight of the sulphiding agent, typically from 0.1 to 0.5% by weight.

Surprisingly, the activity of the hydrotreating catalysts sulphided with a sulphiding agent according to the invention is significantly improved in comparison with the activity of the hydrotreating catalysts sulphided with DMDS.

The sulphiding agent according to the invention can in particular be used for the "in situ" presulphidation of the hydrotreating catalysts including a support based on at least one oxide of a metal or of a semimetal and at least one active metal; in this case, it can, for example, be introduced as a mixture with a gas oil, under a hydrogen pressure which can range from atmospheric pressure up to 20 MPa but is preferably between 1 and 5 MPa, the pressure range commonly used industrially. This stage is carried out at a temperature which can range up to 350° C. (a higher temperature makes it possible to reduce the sulphiding time but very significantly increases the risk of coking).

It is advantageous to carry out this stage in two steps:
 a primary sulphidation carried out at a temperature ranging from 150 to 250° C., preferably from 210 to 230° C., so as to minimize the time necessary for the H$_2$S breakthrough to be obtained in the outlet gases without risking a premature reduction, followed by a secondary sulphidation carried out at a temperature ranging from 250 to 350° C., preferably from 290 to 330° C., and with a duration sufficient to have a constant concentration of H$_2$S in the outlet gases.

The hydrogen blanket, expressed by the ratio of the flow rate by volume of hydrogen in standard liters to the flow rate by volume of the gas oil in liters, is generally between 50 and 500 Sl/l, preferably between 100 and 300 Sl/l.

The hourly space velocity (HSV), defined as the ratio of the hourly flow by volume of gas oil to the volume of catalyst, can range from 0.1 to 5 h$^{-1}$ and is preferably between 1 and 3 h$^{-1}$, a range commonly used industrially.

The total amount of sulphur introduced by the novel sulphiding agent of the invention can generally range from 100 to 250% of the weight of sulphur stoichiometrically required for the complete conversion to sulphides of the oxides of the catalyst.

The sulphiding agent according to the invention can also be used for an "ex situ" presulphidation.

The incorporation of the sulphur in the catalyst is carried out by bringing the catalyst into contact in the absence of hydrogen and makes it possible to obtain the expected degree of sulphidation with great accuracy. This incorporation is generally carried out at a temperature of between 0 and 50° C., preferably between 0 and 30° C. and advantageously at ambient temperature.

The sulphiding agent is generally employed diluted in an appropriate solvent which depends in particular on the nature of the sulphiding agent.

The solvent can be chosen from the following solvents, alone or as a mixture:

light petrol boiling between approximately 60 and 95° C., petrol of hexane type boiling between approximately 63 and 68° C., petrol of type F boiling between approximately 100 and 160° C. and generally comprising 10 to 20% of aromatic hydrocarbons, petrol of white spirit type boiling between approximately 150 and 250° C. and generally comprising 14 to 22% of aromatic hydrocarbons, any hydrocarbon or non-hydrocarbon fraction equivalent to the preceding petrols.

In the examples below, the decomposition temperatures of DEDS and DMDS employed in a catalyst sulphidation process are shown and the solid deposits, in particular related to sulphur, generated by the presence of DEDS according to the invention or of a polysulphide conventionally used as sulphiding agent (di(tert-butyppolysulphide) are measured.

Example 3 shows the improvement in the activity of the hydrotreating catalysts by sulphidation with DEDS to which a scenting base has been added in comparison with sulphidation with DMDS to which the same scenting base has been added.

Example 1

40 cm$^3$ of a commercial hydrotreating catalyst of CoMo type in the oxide form are introduced into a reactor equipped with a temperature probe which makes it possible to determine the temperature within the catalyst. The reactor is placed in an oven which makes it possible to sweep a large temperature range which can be up to 300° C.

A non-desulphurized gas oil of SRGO (Straight Run Gas Oil) type has added to it 0.8% of sulphur contributed by a sulphiding agent, either DMDS or DEDS. The additivated gas oil is subsequently introduced at ambient temperature with a flow rate of 80 cm$^3$/h under a hydrogen flow rate of 20 l/h. Subsequently, the temperature of the oven is adjusted in order to reach 150° C. in the catalyst bed. The gas oil flow rate and the hydrogen flow rate remain fixed respectively at 80 cm$^3$/h and 20 l/h. The gaseous effluents at the reactor outlet are analysed by chromatography in order to monitor the change in the H$_2$S concentration representative of the decomposition of the sulphiding agent. Once a stable H$_2$S concentration value is obtained at 150° C., i.e. [H$_2$S]$_{T=150°C}$, the temperature of the catalyst bed is increased by 10° C. in order to determine the H$_2$S equilibrium concentration at 160° C., i.e. [H$_2$S]$_{T=160°C}$. This operation is repeated by increasing the temperature in steps of 10° C. until temperatures are reached where the H$_2$S concentration remains stable and at a maximum, i.e. [H$_2$S]$_{max}$. The H$_2$S concentration is thus known at each intermediate temperature, i.e. [H$_2$S]$_T$. The degree of decomposition of the sulphiding agent at a temperature T is expressed in % as the ratio [H$_2$S]$_T$/[H$_2$S]$_{max}$×100.

The degrees of decomposition of the dimethyl disulphide and the diethyl disulphide are combined in the table below:

|  | Temperature (° C.) | | | |
| --- | --- | --- | --- | --- |
|  | 150 | 200 | 240 | 250 |
| Degree of decomposition of the sulphiding agent = DMDS (%) | 0 | 31 | 66 | 100 |
| Degree of decomposition of the sulphiding agent = DEDS (%) | 2.5 | 53 | 99 | 100 |

It is found that the DEDS decomposes at a lower temperature than the DMDS.

Example 2

A pipe made of Incolloy 800HT with a length of 30 cm and a diameter of 7.7 cm is placed in an oven in order to vary the temperature inside the pipe between 200 and 400° C. A sulphiding agent is introduced into the pipe as a mixture with nitrogen in order to have a sulphur injection flow rate of 0.8 g of sulphur/h and a nitrogen flow rate of 4 l/h. The sulphiding agent is thus introduced for 3 hours. The effluents at the outlet of the pipe are condensed and recovered. After injecting for 3 hours, the condensates recovered are filtered and, if appropriate, the solid recovered is weighed.

The various sulphiding agents tested are DMDS, DEDS, DPDS, DBDS and a di(tert-butyl) polysulphide sold by Arkema under the name TPS54. The results obtained are presented in the table below:

|  | Sulphiding agent | | | | |
| --- | --- | --- | --- | --- | --- |
|  | TPS54 | DMDS | DEDS | DPDS | DBDS |
| Temperature (° C.) | 350 | 350 | 350 | 350 | 350 |
| Solid deposit (g) | 1.8 | 0 | 0 | 0 | 0 |

On looking at these results, it is apparent that not one of DEDS, DPDS or DBDS forms a solid deposit, in contrast to TPSS4. These measurements confirm the possible formation of a solid deposit observed industrially when polysulphides are employed as sulphiding agent.

Example 3

An activity test was carried out on a pilot-scale hydrotreating plant in order to compare the activity of DMDS to which 3000 ppm of an odour-masking agent have been added with that of DEDS to which 3000 ppm of the same masking agent have been added. This pilot-scale plant represents an industrial hydrotreating unit. The reactor is charged with a commercial catalyst of Nickel Molybdenum (NiMo) type supported on alumina. The reactor has a volume of 300 ml, a diameter of 17.4 mm and a height of 1300 mm. The catalyst is charged between two layers of carborundum, an inert silicon carbide material, ensuring better distribution of the fluids. The volume of catalyst charged is 20 ml. The sulphidation feedstock used is a gas oil resulting from the atmospheric distillation of crude oil (Straight Run Gas Oil: SRGO) to which 1% of sulphur coming from the sulphiding agent has been added. As DMDS and DEDS do not have the same sulphur content, this procedure makes it possible to compare comparable aspects. The sulphidation was carried out under a pressure of 4.5 MPa, an hourly space velocity (HSV) of 1 h$^{-1}$ and an H$_2$/hydrocarbon (HC) ratio of 200 Sl/l in the following way:

- Rise in temperature from 150° C. to 230° C. at the rate of 25° C./h under the sulphidation feedstock.
- Continuous monitoring of the content of H$_2$S and other mercaptans in the gases exiting from the reactor.
- Temperature stationary phase at 230° C. maintained for 4 h (which makes it possible to achieve an H$_2$S breakthrough of greater than 3000 ppm).
- Rise in temperature from 230° C. to 350° C. at the rate of 25° C./h.
- Stationary phase at 350° C. for 12 h.
- Halting of the sulphidation feedstock and switching to the test feedstock.

The test feedstock used is a mixture of Straight Run Gas Oil (SRGO) and of Light Crude Oil (LCO) in a 70/30 ratio having a total sulphur content of 10 400 ppm.

The desulphurization test is subsequently carried out at different temperatures (340° C., 350° C. and 360° C.) with periods of stabilization in order to determine the effectiveness of the sulphided catalyst.

The total sulphur content in the feedstock after passing through the hydrotreating reactor is determined continuously during the desulphurization test.

The odour-masking agent has the following composition by weight: isoamyl acetate (25%), diethyl orthophthalate (50%), 2-methylbutyl butyrate (15%) and benzyl acetate (10%).

The results are presented in FIG. 1:

It is found that the additivated DEDS makes it possible to obtain the same level of desulphurization (10 ppm) as the additivated DMDS but with 5° C. less (353° C. instead of 358° C.), which is highly significant for a hydrotreating unit.

The invention claimed is:

1. A method of hydrotreating a hydrocarbon material to reduce its sulphur content which comprises
    contacting the hydrocarbon material with a hydrotreating catalyst comprising an active metal catalyst supported on a catalyst base of an oxide of a metal or semi-metal, said hydrotreating catalyst having been presulphided with a sulphiding agent consisting essentially of diethyl disulphide (DEDS) dissolved in a solvent composition consisting essentially of a solvent selected from the group consisting of light or heavy petrols, alkanes, aromatic hydrocarbons, and hydrocarbon or non-hydrocarbon fractions thereof, and optionally 0.1 to 1% by weight of at least one odour-masking agent,
    wherein the hydrotreating catalyst achieves the same level of desulphurization at a lower temperature than the same catalyst presulphided with dimethyl disulphide (DMDS).

2. The method of claim 1, wherein the hydrotreating catalyst was presulphided in situ.

3. The method of claim 2, wherein the hydrotreating catalyst was presulphided by contacting the sulphiding agent with the hydrotreating catalyst under a hydrogen pressure at a temperature of up to 350° C.

4. The method of claim 2, wherein the hydrotreating catalyst was presulphided in two stages comprising a primary sulphidation stage wherein the sulphiding agent is contacted with the hydrotreating catalyst at a temperature ranging from 150 to 250° C., followed by a secondary sulpidation stage wherein the sulphiding agent is contacted with the hydrotreating catalyst at a temperature ranging from 250 to 350° C.

5. The method of claim 4, wherein the hydrotreating catalyst was presulphided under a pressure of 4.5 MPa, an hourly space velocity of 1 h$^{-1}$, and an H$_2$/hydrocarbon ratio of 200 Sl/l.

6. The method of claim 1, wherein the hydrotreating catalyst was presulphided ex situ.

7. The method of claim 6, wherein the hydrotreating catalyst was presulphided by contacting the sulphiding agent with the hydrotreating catalyst in the absence of hydrogen at a temperature between 0 and 50° C.

8. A method of presulphiding a hydrotreating catalyst comprising an active metal catalyst supported on a catalyst base of an oxide of a metal or semi-metal, which comprises
    contacting the hydrotreating catalyst with a sulphiding agent consisting essentially of diethyl disulphide (DEDS) dissolved in a solvent composition consisting essentially of a solvent selected from the group consisting of light or heavy petrols, alkanes, aromatic hydrocarbons, and hydrocarbon or non-hydrocarbon fractions thereof, and optionally 0.1 to 1% by weight of at least one odour-masking agent,
    wherein, when used in a method of hydrotreating a hydrocarbon material to reduce its sulphur content, the hydrotreating catalyst is able to achieve the same level of desulphurization at a lower temperature than the same catalyst presulphided with dimethyl disulphide (DMDS).

9. The method of claim 8, wherein the hydrotreating catalyst is presulphided in situ.

10. The method of claim 8, wherein the hydrotreating catalyst is presulphided ex situ.

11. The method of claim 8, which comprises contacting the hydrotreating catalyst with the sulphiding agent under a hydrogen pressure at a temperature of up to 350° C.

12. The method of claim 8, which comprises contacting the hydrotreating catalyst with the sulphiding agent at a first temperature range of 150 to 250° C., and then at a second temperature range of 250 to 350° C.

13. The method of claim 12, which comprises contacting the hydrotreating catalyst with the sulphiding agent under a pressure of 4.5 MPa, an hourly space velocity of 1 h$^{-1}$, and an H$_2$/hydrocarbon ratio of 200 Sl/l.

14. The method of claim 8, wherein the hydrotreating catalyst was presulphided by contacting the sulphiding agent with the hydrotreating catalyst in the absence of hydrogen at a temperature between 0 and 50° C.

15. A method of decreasing the desulphurization temperature required for hydrotreating a hydrocarbon material to reduce its sulphur content which comprises contacting the hydrocarbon material with a hydrotreating catalyst comprising an active metal catalyst supported on a catalyst base of an oxide of a metal or semi-metal, said hydrotreating catalyst having been presulphided with diethyl disulphide (DEDS) instead of dimethyl disulphide (DMDS), wherein the hydrotreating catalyst achieves the same level of desulphurization at a lower temperature than the same catalyst presulphided with DMDS.

16. A method of hydrotreating a hydrocarbon material to reduce its sulphur content which comprises contacting the hydrocarbon material with a hydrotreating catalyst comprising an active metal catalyst supported on a catalyst base of an oxide of a metal or semi-metal, said hydrotreating catalyst having been presulphided with a sulphiding agent consisting essentially of diethyl disulphide (DEDS) dissolved in a solvent composition consisting essentially of a solvent selected from the group consisting of light or heavy petrols, alkanes, aromatic hydrocarbons, and hydrocarbon or non-hydrocarbon fractions thereof, and optionally 0.1 to 1% by weight of at least one odour-masking agent, wherein the hydrotreating catalyst outperforms the same catalyst presulphided with DMDS, with respect to desulphurization, across a temperature range of 340° C. to 360° C.

17. The method of claim 16, wherein the hydrotreating catalyst outperforms the same catalyst presulphided with DMDS, with respect to desulphurization, across the entire temperature range of 340° C. to 360° C.

18. The method of claim 16, wherein the hydrotreating catalyst was presulphided by contacting the sulphiding agent with the hydrotreating catalyst under a hydrogen pressure at a temperature of up to 350° C.

19. The method of claim 16, wherein the hydrotreating catalyst was presulphided in two stages comprising a primary sulphidation stage wherein the sulphiding agent is contacted with the hydrotreating catalyst at a temperature ranging from 150 to 250° C., followed by a secondary sulpidation stage wherein the sulphiding agent is contacted with the hydrotreating catalyst at a temperature ranging from 250 to 350° C.

20. The method of claim 18, wherein the hydrotreating catalyst was presulphided under a pressure of 4.5 MPa, an hourly space velocity of 1 $h^{-1}$, and an $H_2$/hydrocarbon ratio of 200 Sl/l.

* * * * *